United States Patent [19]
Wakita et al.

[11] Patent Number: 5,154,858
[45] Date of Patent: Oct. 13, 1992

[54] NONLINEAR OPTICAL COMPOUND

[75] Inventors: Katsuya Wakita, Nara; Nobuo Sonoda, Settsu; Hisashi Minemoto, Kyoto; Tetsuji Kawakami, Katano; Tatsurou Kawamura, Takatsuki; Yusuke Ozaki, Toyonaka, all of Japan

[73] Assignee: Matsushita Electric Industrial Co., Ltd., Osaka, Japan

[21] Appl. No.: 794,884

[22] Filed: Nov. 20, 1991

[30] Foreign Application Priority Data

Nov. 22, 1990 [JP] Japan .................... 2-318724

[51] Int. Cl.[5] ............... F21V 9/04; C07D 233/54
[52] U.S. Cl. ..................... 252/582; 252/587; 252/589; 359/328; 548/125; 548/354.1
[58] Field of Search ........ 252/582, 587, 589, 99.01; 548/125, 126, 375, 341, 346, 347; 359/328, 242

[56] References Cited

U.S. PATENT DOCUMENTS

| | | | |
|---|---|---|---|
| 4,728,576 | 3/1988 | Gillberg-LaForce et al. | 128/411.1 |
| 4,773,743 | 9/1988 | Choe et al. | 359/393 |
| 4,886,339 | 12/1989 | Scozzafava et al. | 385/141 |
| 4,977,201 | 12/1990 | Ogawa et al. | 523/400 |
| 4,981,614 | 1/1991 | Miyazaki et al. | 252/587 |

OTHER PUBLICATIONS

Chemical Abstracts 80:4841z (1974).
Bree et al., Mol. Cryst. Liq. Cryst., vol. 186, pp. 99–105 (1990).
Hewig et al., Optics Communications, vol. 47, No. 5, pp. 347–350 (1983).

*Primary Examiner*—Robert L. Stoll
*Assistant Examiner*—Shean C. Wu
*Attorney, Agent, or Firm*—Wenderoth, Lind & Ponack

[57] ABSTRACT

A nonlinear optical compound of the formula:

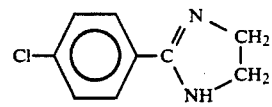

and optionally a $\pi$ electron conjugated organic compound having an electron donative group and an electron attractive group, which has high conversion efficiency.

5 Claims, 1 Drawing Sheet

NONLINEAR OPTICAL COMPOUND

BACKGROUND OF THE INVENTION

1. Field of the Invention

The present invention relates to a nonlinear optical compound which can be used in various optical devices such as a high speed optical switch and an optical memory.

2. Background of the Invention

As a photonics material for optical devices, a compound or a material which has a large nonlinear optical effect and high speed response is desired, and a wide variety of compounds or materials are studied.

As such compound, an organic compound having a $\pi$ electron conjugated system is considered to be better than a crystalline inorganic material in which lattice vibration contributes to the nonlinear optical effect. To design such organic compound, it is generally and strongly proposed to introduce at least one strong donor type (electron donative) group and at least one acceptor type (electron attractive) group in a molecular having the $\pi$ electron system.

Alternatively, to introduce an organic compound which exhibits strong nonlinear optical characteristics in a polymer, there are proposed a method comprising crystallizing a compound each molecule of which has a large dipole moment while controlling molecular orientation by applying an electric field so as to exhibit the nonlinear optical characteristics more effectively (Japanese Patent Kokai Publication Nos. 274122/1989 and 188835/1989), a method comprising introducing a nonlinear optical material in side chains of a polymer, and a method comprising crosslinking such compound with polymer chains through a chemical reaction between the compound molecules and the polymer chains.

However, in case of the organic compound having the $\pi$ electron conjugated system in which the strong electron donative and electron attractive groups are introduced, its crystallization is difficult, or if it is crystallized, the nonlinear optical characteristics are not realized because, due to a very large dipole moment, the compound is crystallized with compensating the dipole moments of the molecules each other.

When a $\pi$ electron conjugate length is elongated, an absorption edge of the material shifts to a long wavelength side, so that the material absorbs a fundamental wave and higher harmonics, whereby an output is decreased.

SUMMARY OF THE INVENTION

One object of the present invention is to provide a nonlinear optical compound having good nonlinear optical characteristics and an absorption edge in a shorter wavelength range.

Another object of the present invention is to provide a second harmonic generation device having improved properties.

According to one aspect of the present invention, there is provided a nonlinear optical compound of the formula:

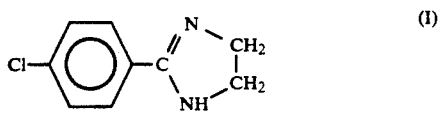

(I)

According to the second aspect of the present invention, there is provided a nonlinear optical composition comprising the nonlinear optical compound (I) and a $\pi$ electron conjugated organic compound having an electron donative group and an electron attractive group.

According to the third aspect of the present invention, there is provided a second harmonic generation device comprising the nonlinear optical compound (I) or the nonlinear optical composition which comprises the compound (I) and the $\pi$ electron conjugated organic compound having an electron donative group and an electron attractive group.

Since the compound (I) has a shorter $\pi$ electron conjugate length, its absorption edge shifts to a shorter wavelength side and therefore it does not absorb the higher harmonic, whereby the nonlinear optical characteristics are effectively exhibited.

Though the $\pi$ electron conjugated organic compound having an electron donative group and an electron attractive group is expected to have good nonlinear optical characteristics in a molecule level, it does not exhibit nonlinear optical characteristics as a whole due to its centrosymmetric structure. But, according to the second aspect of the present invention, when such $\pi$ electron conjugated organic compound is used in combination with the nonlinear optical compound (I) of the present invention, the composition exhibits the nonlinear optical characteristics.

DETAILED DESCRIPTION OF THE INVENTION

Figure 1:
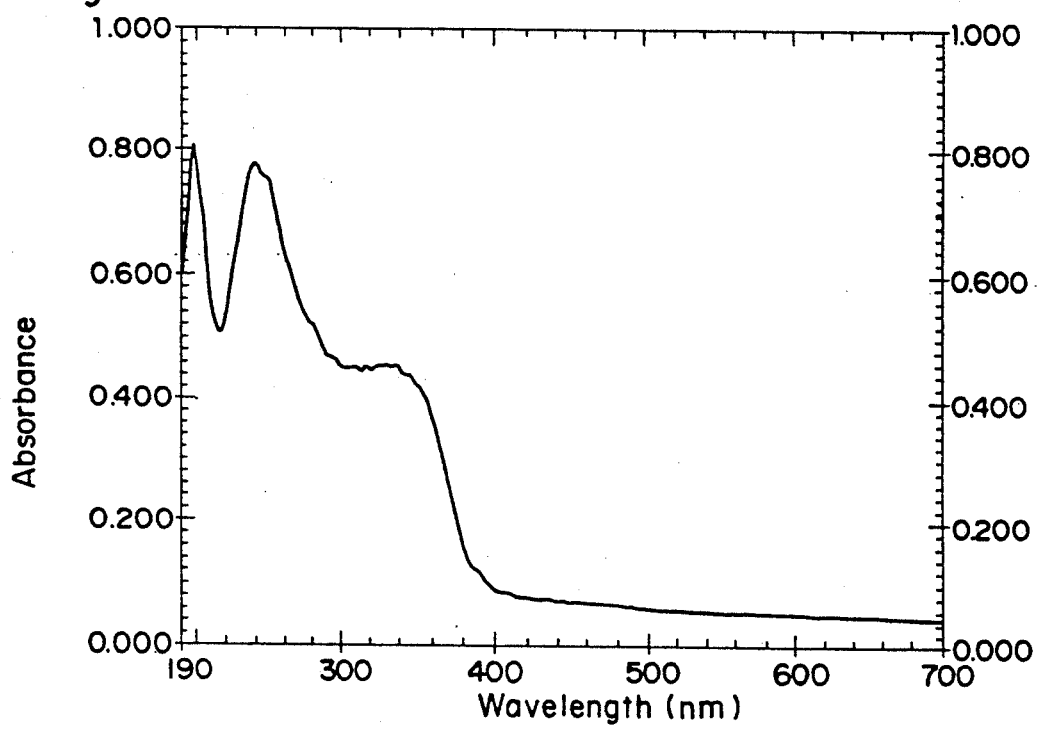
FIG. 1 shows absorbance of 2-(p-chlorophenyl)imidazoline in the UV-visible light range.

In present invention, since the nonlinear optical organic compound (I) has good nonlinear optical characteristics, it can be used alone as the nonlinear optical material. Alternatively, the compound (I) can be used in combination with the $\pi$ electron conjugated organic compound having an electron donative group and an electron attractive group so that the nonlinear optical characteristics of both compounds are effectively exhibited.

Examples of the electron donative group are —OH, —OCH$_3$, —OCOCH$_3$, —NH$_2$, —N(CH$_3$)$_3$, —NHCOCH$_3$, alkyl groups such as a methyl group, aryl groups such as a phenyl group, and the like.

Examples of the electron attractive group are —NH$_3$, —CF$_3$, —CCl$_3$, —NO$_2$, —CN, —CHO, COCH$_3$, —CO$_2$C$_2$H$_5$, —COOH, —SO$_2$CH$_3$, —SO$_3$H, —F, —Cl, —Br, —I, —CH$_2$Cl, —CH=CHNO$_2$, and the like. Among them, a cyano (—CN) group is preferred, since it will easily shift the absorption edge to a shorter wavelength side.

Preferred examples of the $\pi$ electron conjugated organic compound having an electron donative group and an electron attractive group are nitroaniline compounds (e.g. p-nitroaniline, N-(p-nitrophenyl)ethylenediamine, di(p-nitrophenyl)ethylenediamine, etc.), other aromatic cyclic compounds such as aniline derivatives (e.g. p-cyanoaniline, etc.), conjugated olefin compounds such as stilbene compound derivatives or benzalacetophenone derivatives having an electron donative group and an electron attractive group, heterocyclic compounds such as benzooxadiazole derivatives or nitropyridine derivatives having an electron donative group and an electron attractive group, and Schiff base compounds having an aromatic rings such as benzylideneaniline derivatives. Specific examples are 1,4-substituted naphthalene derivatives having an electron donative group and an electron attractive group, 4-dimethylamino-4-stilbene, 3-(4-methoxyphenyl)-1-(4-aminophenyl)-2-propen-1-one, benzalacetophenone (chalcone) derivatives having an electron donative group and an electron attractive group, 4-nitro-7-chlorobenzooxadiazole, 4'-nitrobenzylidene-3-acetylamino-4-methoxyaniline, N-(4-pyridinylmethylene)-4-dimethylaminobenzenamine dimethylsulfate, N-[2-(5-nitrofurfurylidene)]-4-methoxybenzenamine and the like as well as their analogues.

Preferably, the nonlinear optical composition of the present invention comprises 20 to 80 % by mole of the compound (I) and 80 to 20 % by mole of the $\pi$ electron conjugated organic compound having an electron donative group and an electron attractive group. The composition may be prepared by mixing the compound (I) and the $\pi$ electron conjugated organic compound having an electron donative group and an electron attractive group, melting the mixture and then cooling and soidifying it.

The nonlinear optical compound (I) or its composition with the $\pi$ electron conjugated organic compound having an electron donative group and an electron attractive group may be dispersed in a polymer to form a nonlinear optical material, whereby processability of the material is improved. Since such material comprising the polymer can be formed by coating or spin coating, a thin film article can be easily produced. In this case, heat generation due to absorption can be suppressed since the absorption edge of the organic compound (I) is in the short wavelength range. Thereby, stability of the crystal structure of the compound (I) is much improved in the state exhibiting second harmonic generation (SHG), and an absorption edge of the composition can be shifted to the shorter wavelength side.

When the nonlinear optical compound (I) or its composition with the $\pi$ electron conjugated organic compound having an electron donative group and an electron attractive group is dispersed in the polymer, an amount of the compound (I) or the composition is about 5 to 20 % by weight based on the weight of the composition.

Preferred examples of the polymer in which the compound (I) or its composition is dispersed are polyethyleneoxide, polyvinyl alcohol, polymethyl methacrylate, polyvinylacetal, epoxy resin and the like. The compound (I) or its composition may be dispersed in the polymer by dissolving it in a solvent (e.g. methanol, etc.) and mixing with the polymer, whereby the compound (I) and/or the $\pi$ electron conjugated organic compound having an electron donative group and an electron attractive group are uniformly dispersed in the polymer.

PREFERRED EMBODIMENTS OF THE INVENTION

The present invention will be illustrated by following Examples.

EXAMPLE 1

2-(p-Chlorophenyl)imidazoline used in the Examples was prepared by the process of Oxley et al disclosed in J. Chem. Soc., 497–505, 1947 as follows:

In a 2 liter three-necked flask, ethylene diamine (160 g) was charged while stirring. After adding cupric acid (10 g) as a catalyst, p-cyanochlorobenzene (87 g) was gradually added, and a reaction was continued while heating the flask on an oil bath at 120 to 130° C for about three hours. Then, the flask was cooled to room temperature, pure water (1 liter) was added to the mixture in the flask, and the mixture was kept standing one day.

The formed precipitate was filtered and heated in boiling water, followed by filtration. Then, the filtrate was recrystallized with ethyl acetate to obtain white crystalline powder 2-(p-chlorophenyl)imidazoline. The results of elemental analysis were as follows:

|  | C | H | N (%) |
| --- | --- | --- | --- |
| Measurement 1: | 60.49 | 5.15 | 15.77 |
| Measurement 2: | 60.44 | 5.15 | 15.68 |
| Average: | 60.47 | 5.15 | 15.73 |

The resulting compound was also identified as 2-(p-chlorophenyl)imidazoline by its melting point (186° C.), mass spectrum (molecular weight of 180) and IR spectrum.

When a laser beam of Nd:YAG laser (1064 nm) was irradiated on white crystalline powder of 2-(p-chlorophenyl)imidazoline, SHG having substantially the same intensity as urea was observed.

The absorption edge was at less than 400 nm as seen from the absorbance in the solid state measured by an integrating sphere of UV-visible light spectrometry shown in FIG. 1.

EXAMPLE 2

A mixture of white crystalline powder 2-(p-chlorophenyl)imidazoline and p-cyanoaniline in a molar ratio of 1:1 was heated and molten at 180° C. and cooled to solidify it. When, on the resulting composition, the same laser beam as used in Example 1 was irradiated, SHG having a several times larger intensity than urea was observed.

Figure 2:
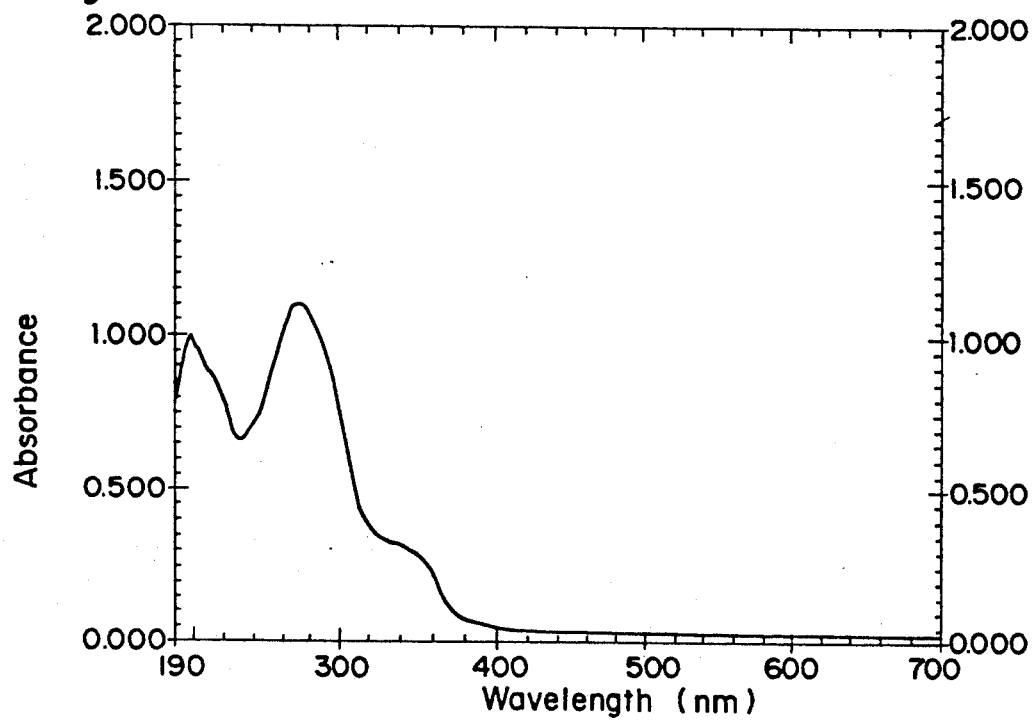
FIG. 2 shows absorbance of a composition of 2-(p-chlorophenyl)imidazoline and p-cyanoaniline in the UV-visible light range.

The absorbance of the composition in the UV-visible light range is shown in FIG. 2.

EXAMPLE 3

Polyethyleneoxide (hereinafter referred to as "PEO") (5 g) was dissolved in methanol (100 ml) with stirring to obtain a homogeneous PEO solution. In the PEO solution, white crystalline powder 2-(p-chlorophenyl)imidazoline (1 g) was dissolved to obtain a homogeneous solution which was applied on a glass plate by spin coating, followed by heating at 60° C. to evaporate methanol. When the same laser beam as used in Example 1 was irradiated on a thin film of the mixture of PEO and 2-(p-chlorophenyl)imidazoline, SHG was observed.

When an electric field is applied during the evaporation of methanol, the orientation of the molecules is improved and the intensity of SHG is increased.

EXAMPLE 4

White crystalline powder 2-(p-chlorophenyl)imidazoline was charged in a crucible of an evaporation apparatus and heated and evaporated under reduced pressure of $10^{-7}$ Torr to deposit it on a glass plate to a film thickness of 1 μm.

When the same laser beam as used in Example 1 was irradiated on the formed thin film, SHG was observed.

What is claimed is:

1. A nonlinear optical composition comprising a compound of the formula:

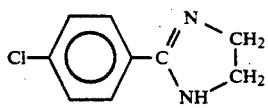

(I)

and a π electron conjugated organic compound having an electron donative group and an electron attractive group.

2. The nonlinear optical composition according to claim 1, wherein said π electron conjugated compound is an aromatic cyclic compound or a hetero-aromatic cyclic compound.

3. The nonlinear optical conjugated compound according to claim 1, wherein said electron attractive group is a cyano group.

4. A second harmonic generation device which comprises a compound of the formula:

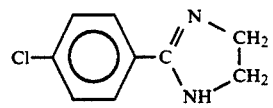

(I)

5. A second harmonic generation device which comprises a nonlinear optical composition comprising a compound of the formula:

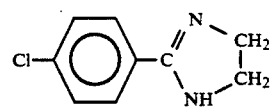

(I)

and a π electron conjugated organic compound having an electron donative group and an electron attractive group.

* * * * *